(12) United States Patent
Yamazaki et al.

(10) Patent No.: US 7,790,903 B2
(45) Date of Patent: Sep. 7, 2010

(54) PROCESS FOR PRODUCTION OF OPTICALLY ACTIVE PPAR-ACTIVATING COMPOUND AND INTERMEDIATE OF THE SAME

(75) Inventors: Yukiyoshi Yamazaki, Higashimurayama (JP); Takaaki Araki, Higashimurayama (JP); Minoru Koura, Kawagoe (JP); Kimiyuki Shibuya, Tokorozawa (JP)

(73) Assignee: Kowa Co., Ltd., Nagoya-shi (JP)

( * ) Notice: Subject to any disclaimer, the term of this patent is extended or adjusted under 35 U.S.C. 154(b) by 449 days.

(21) Appl. No.: 11/816,472

(22) PCT Filed: Feb. 23, 2006

(86) PCT No.: PCT/JP2006/303245

§ 371 (c)(1),
(2), (4) Date: Aug. 16, 2007

(87) PCT Pub. No.: WO2006/090768

PCT Pub. Date: Aug. 31, 2006

(65) Prior Publication Data

US 2008/0194833 A1 Aug. 14, 2008

(30) Foreign Application Priority Data

Feb. 23, 2005 (JP) ............... 2005-047476

(51) Int. Cl.
*C07D 263/58* (2006.01)
(52) U.S. Cl. ................................... 548/222
(58) Field of Classification Search ............ 548/222
See application file for complete search history.

(56) References Cited

U.S. PATENT DOCUMENTS

| 7,109,226 B2 | 9/2006 | Yamazaki et al. |
| 7,183,295 B2 | 2/2007 | Yamazaki et al. |
| 2005/0101636 A1* | 5/2005 | Yamazaki et al. ......... 514/338 |

FOREIGN PATENT DOCUMENTS

| JP | 2004 210776 | 7/2004 |
| WO | 02 46176 | 6/2002 |
| WO | 2005 023777 | 3/2005 |
| WO | WO 2005/023777 A1 | 3/2005 |

OTHER PUBLICATIONS

Clive, et al., "Formal Radical Cyclization onto Benzene Rings: A General Method and Its Use in the Synthesis of ent-Nocardione A", Journal of Organic Chemistry, vol. 69, No. 10, pp. 3282-3293, 2004.
Effenberger, et al., "Aminosaeuren, 5¹ Stereoselektive Synthesen Von a,a'-Iminodicarbonsaeuren", Liebigs Ann. Chem. No. 2, pp. 334-358, 1986.
U.S. Appl. No. 11/816,921, filed Aug. 23, 2007, Yamazaki, et al.
U.S. Appl. No. 11/912,811, filed Oct. 26, 2007, Yamazaki, et al.

(Continued)

Primary Examiner—Rebecca L Anderson
Assistant Examiner—Jason M Nolan
(74) Attorney, Agent, or Firm—Oblon, Spivak, McClelland, Maier & Neustadt, L.L.P.

(57) ABSTRACT

A process for obtaining a compound (1) and an intermediate thereof in high yield and high optical yield is provided.

A process for producing a compound (4), the process including reacting a compound (2) with a compound (3) in the presence of a base; and a process for producing a compound (1), the process including reacting a compound (2) with a compound (3) in the presence of a base to yield a compound (4) and then deesterifying the compound (4).

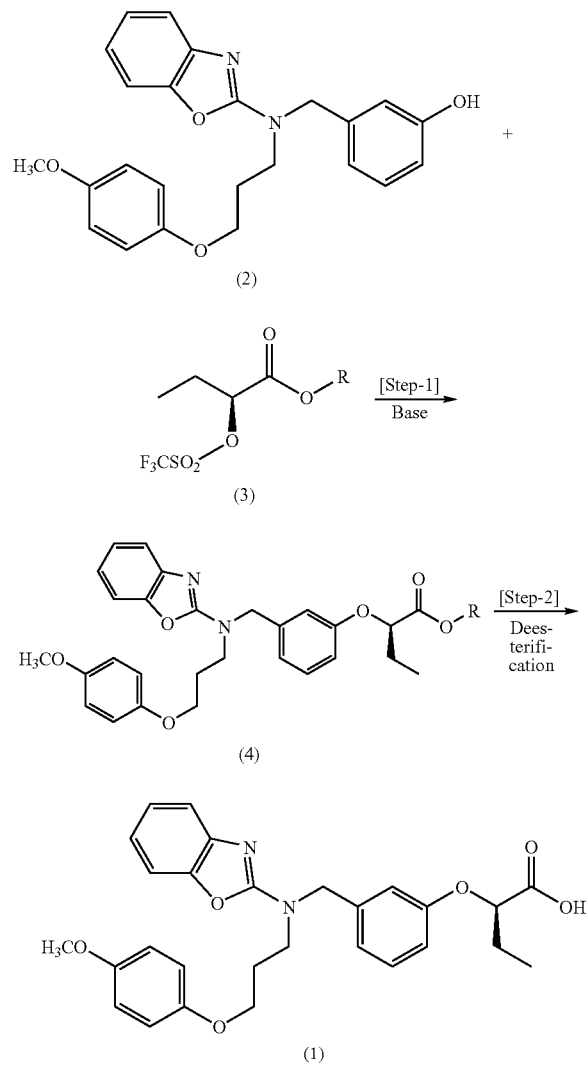

wherein R represents an alkyl group having 1 to 6 carbon atoms or an aralkyl group having 7 to 8 carbon atoms.

15 Claims, No Drawings

OTHER PUBLICATIONS

Isabelle Issemann, et al., "Activation of a member of the steroid hormone receptor superfamily by peroxisome proliferators", Nature, vol. 347, Oct. 18, 1990, pp. 645-650.

Christine Dreyer, et al., "Control of the Peroxisomal β-Oxidation Pathway by a Novel Family of Nuclear Hormone Receptors", Cell, vol. 68, Mar. 6, 1992, pp. 879-887.

"A Unified Nomenclature System for the Nuclear Receptor Superfamily", Letter to the Editor, Cell, vol. 97, Apr. 16, 1999, pp. 161-163.

Kristina Schoonjans, et al. "The peroxisome proliferator activated receptors (PPARs) and their effects on lipid metabolism and adipocyte differentiation", Biochimica et Biophysica Acta 1302, 1996, pp. 930-109.

Timothy M. Willson, et al., "The PPARs: From Orphan Receptors to Drug Discovery", Journal of Medicinal Chemistry, vol. 43, No. 4, Feb. 24, 2000, pp. 527-550.

Frank J. Gonzalez, et al., "Mechanism of Action of the Nongenotoxic Peroxisome, Proliferators:Role of the Peroxisome Proliferator-Activated Receptor α", Journal of the National Cancer Institute, vol. 90. No. 22, Nov. 22, 1998, pp. 1702-1709.

Jean-Charles Fruchart, et al., "Peroxisome proliferator-activated receptor-alpha activators regulate genes governing lipoprotein metabolism, vascular inflammation and atherosclerosis", Current Opinion in Lipidology, 1999, pp. 245-257.

Johan Auwerx, et al., "Regulation of Triglyceride Metabolism by PPARs : Fibrates and Thiazolidinediones have Distinct Effects", Journal of Atherosclerosis and Thrombosis, vol. 3, No. 2, 1996, pp. 81-89.

Bart Staels, et al., "Role of PPAR in the Pharmacological Regulation of Lipoprotein Metabolism by Fibrates and Thiazolidinediones", Current Pharmaceutical Design, 3, 1997, pp. 1-14.

Inés Pineda, et al., "Peroxisome proliferator-activated receptor alpha in metabolic disease, inflammation, atherosclerosis and aging", Current Opinion in Lipidology, 1999, pp. 151-159.

Joseph Vamecq, et al., "Medical significance of peroxisome proliferator-activated receptors", The Lancet, vol. 354, Jul. 10, 1999, pp. 141-148.

Sander J. Robins, "PPAR aligands and clinical trials: cardiovascular risk reduction with fibrates", Journal of Cardiovascular Risk, vol. 8, No. 4, 2001, pp. 195-201.

Naoki Sakane, et al., "Glitazones and NIDDM", The Lancet, vol. 349, 1997, p. 952.

Jennifer L. Oberfield, et al., "A peroxisome proliferator-activated receptor γ ligand inhibits adipocyte differentiation", Proc. Natl. Acad. Sci., vol. 96, Biochemistry, May 1999, pp. 6102-6106.

Harold M. Wright, et al., "A Synthetic Antagonist for the Peroxisome Proliferator-activated Receptor γ Inhibits Adipocyte Differentiation", The Journal of Biological Chemistry, vol. 275, No. 3, Jan. 21, 2000, pp. 1873-1877.

Toshimasa Yamauchi, et al., "Inhibition of RXR and PPAR γ ameliorates diet-induced obesity and type 2 diabetes", The Journal of Clinical Investigation, vol. 108, No. 7, Oct. 2001, pp. 1001-1013.

Yaacov Barak, et al., "Effects of peroxisome proliferator-activated receptor δ on placentation, adiposity, and colorectal cancer", Proc. Natl. Acad. Sci., vol. 99, No. 1, Jan. 8, 2002, pp. 303-308.

* cited by examiner

PROCESS FOR PRODUCTION OF OPTICALLY ACTIVE PPAR-ACTIVATING COMPOUND AND INTERMEDIATE OF THE SAME

CROSS-REFERENCE TO RELATED APPLICATIONS

The present application is a 35 U.S.C. §371 National Stage patent application of International patent application PCT/JP06/303245, filed on Feb. 23, 2006, which claims priority to Japanese patent application JP 2005-047476, filed on Feb. 23, 2005.

TECHNICAL FIELD

The present invention relates to a process for production of a PPAR (peroxisome proliferators-activated receptor) activating compound which is useful as a prophylactic and/or therapeutic drug for diseases such as hyperlipidemia, arteriosclerosis, diabetes mellitus and the like, and an intermediate of the same.

BACKGROUND ART

PPAR is known as one of nuclear receptor families, and three subtypes (α, γ, δ) thereof are so far known to exist (Non-Patent Documents 1 to 5). Among these, PPARα is mainly expressed in the liver, and is known to be activated by plasticizers and fibrate drugs, for example, Wy14643 or drugs that are already being marketed as pharmaceutical products, such as clofibrate, fenofibrate, bezafibrate, gemfibrozil and the like (Non-Patent Documents 6 to 7).

Activation of PPARα is known to cause an increase in β-oxidation of fatty acids, and a decrease in the blood triglyceride level in mammals, and to reduce the blood lipid such as low density lipoprotein (LDL) cholesterol, very low density lipoprotein (VLDL) cholesterol, and the like, in humans Thus, PPARα activators are believed to be useful as a prophylactic and/or therapeutic agent for hyperlipidemia and the like. Furthermore, since PPARα activators increase high density lipoprotein (HDL) cholesterol, while suppressing the expression of VCAM-1, which is a cell adhesion factor in the blood vessel, the activators are considered to be useful as a prophylactic and/or therapeutic agent for arteriosclerosis and the like, and useful for the prevention and/or treatment of diabetes mellitus, inflammatory diseases, heart diseases and the like (Non-Patent Documents 8 to 14).

Meanwhile, activation of PPARγ causes an increase in fats in humans, and is reported to have an undesirable action of inducing weight increase or obesity (Non-Patent Document 15). Recently, it has been also reported that there is a possibility to improve resistance to insulin by means of PPARγ antagonists (Non-Patent Documents 16 to 18). Also, it is suggested that activation of PPARδ is connected with the action of lipid accumulation (Non-Patent Document 19). Therefore, it is conceived that PPARα-selective activators having low activities for PPARγ and PPARδ are useful as prophylactic and/or therapeutic agents for hyperlipidemia, arteriosclerosis, diabetes mellitus, diabetic complications, inflammation, heart diseases and the like, without being accompanied by weight increase or obesity.

Under such circumstances, the inventors of the present invention found that a compound represented by the following Formula (A):

[Chemical 1]

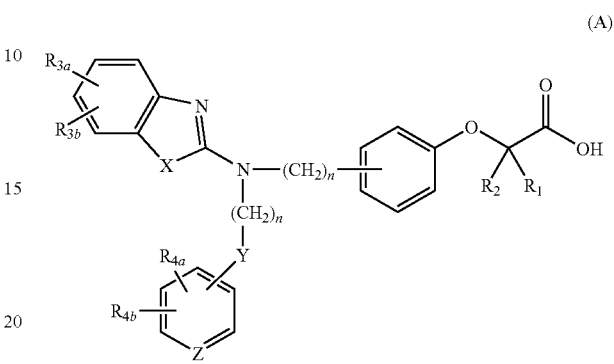

wherein $R_1$ and $R_2$, which may be identical or different, each represent a hydrogen atom, a methyl group or an ethyl group; $R_{3a}$, $R_{3b}$, $R_{4a}$ and $R_{4b}$, which may be identical or different, each represent a hydrogen atom, a halogen atom, a nitro group, a hydroxyl group, a $C_{1-4}$ alkyl group, a trifluoromethyl group, a $C_{1-4}$ alkoxy group, a $C_{1-4}$ alkylcarbonyloxy group, a di-$C_{1-4}$ alkylamino group, a $C_{1-4}$ alkylsulfonyloxy group, a $C_{1-4}$ alkylsulfonyl group, a $C_{1-4}$ alkylsulfinyl group or a $C_{1-4}$ alkylthio group, or alternatively, $R_{3a}$ and $R_{3b}$ or $R_{4a}$ and $R_{4b}$ are bound to represent an alkylenedioxy group; X represents an oxygen atom, a sulfur atom or N—$R_5$ (wherein $R_5$ represents a hydrogen atom, a $C_{1-4}$ alkyl group, a $C_{1-4}$ alkylsulfonyl group or a $C_{1-4}$ alkyloxycarbonyl group); Y represents an oxygen atom, a $S(O)_1$ group (wherein 1 represents a number from 0 to 2), a carbonyl group, a carbonylamino group, an aminocarbonyl group, a sulfonylamino group, an aminosulfonyl group or an NH group; Z represents CH or N; n represents a number from 1 to 6; and m represents a number from 2 to 6, or a salt thereof selectively activates PPARα, thus being useful as a medicine, and filed a patent application (Patent Document 1).

[Patent Document 1] PCT/JP04/012750
[Non-Patent Document 1] Nature, 347, 645-650, 1990
[Non-Patent Document 2] Cell, 68, pp. 879-887, 1992
[Non-Patent Document 3] Cell, 97, pp. 161-163, 1999
[Non-Patent Document 4] Biochim. Biophys. Acta., 1302, pp. 93-109, 1996
[Non-Patent Document 5] Journal of Medicinal Chemistry, 43, pp. 527-550, 2000
[Non-Patent Document 6] Journal of the National Cancer Institute, 90, 1702-1709, 1998
[Non-Patent Document 7] Current Opinion in Lipidology, 10, pp. 245-257, 1999
[Non-Patent Document 8] Journal of Atherosclerosis and Thrombosis, 3, pp. 81-89, 1996
[Non-Patent Document 9] Current Pharmaceutical Design, 3, pp. 1-14, 1997

[Non-Patent Document 10] Current Opinion in Lipidology, 10, pp. 151-159, 1999

[Non-Patent Document 11] Current Opinion in Lipidology, 10, pp. 245-257, 1999

[Non-Patent Document 12] The Lancet, 354, pp. 141-148, 1999

[Non-Patent Document 13] Journal of Medicinal Chemistry, 43, pp. 527-550, 2000

[Non-Patent Document 14] Journal of Cardiovascular Risk, 3, pp. 195-201, 2001

[Non-Patent Document 15] The Lancet, 349, pp. 952, 1997

[Non-Patent Document 16] Proc. Natl. Acad. Sci., 96, pp. 6102-6106, 1999

[Non-Patent Document 17] The Journal of Biological Chemistry, 275, pp. 1873-1877, 2000

[Non-Patent Document 18] J. Clin. Invest., 108, 1001-1013, 2001

[Non-Patent Document 19] Proc. Natl. Acad. Sci., 99, pp. 303-308, 2002

DISCLOSURE OF THE INVENTION

Problems to be Solved by the Invention

It is an object of the present invention to provide a process for producing (R)-2-[3-[N-(benzoxazol-2-yl)-N-(3-(4-methoxyphenoxy)propyl)aminomethyl]phenoxy]butyric acid (compound (1)), which is one of the compounds represented by the above Formula (A), and an intermediate thereof in high yield and high optical yield.

Means to Solve the Problems

The inventors of the present invention devotedly conducted research on a useful process for production of the compound (1) among the compounds represented by the above Formula (A), and as a result, found that, as shown in the following reaction scheme, when optically active 2-trifluoromethanesulfonyloxybutyric acid ester (compound (3)) is etherified with a compound (2) in the presence of a base, a compound (4) is obtained in high yield and high optical purity, and by deesterifying the compound (4), the compound (1) can be produced without impairing the yield and the optical purity.

[Chemical 2]

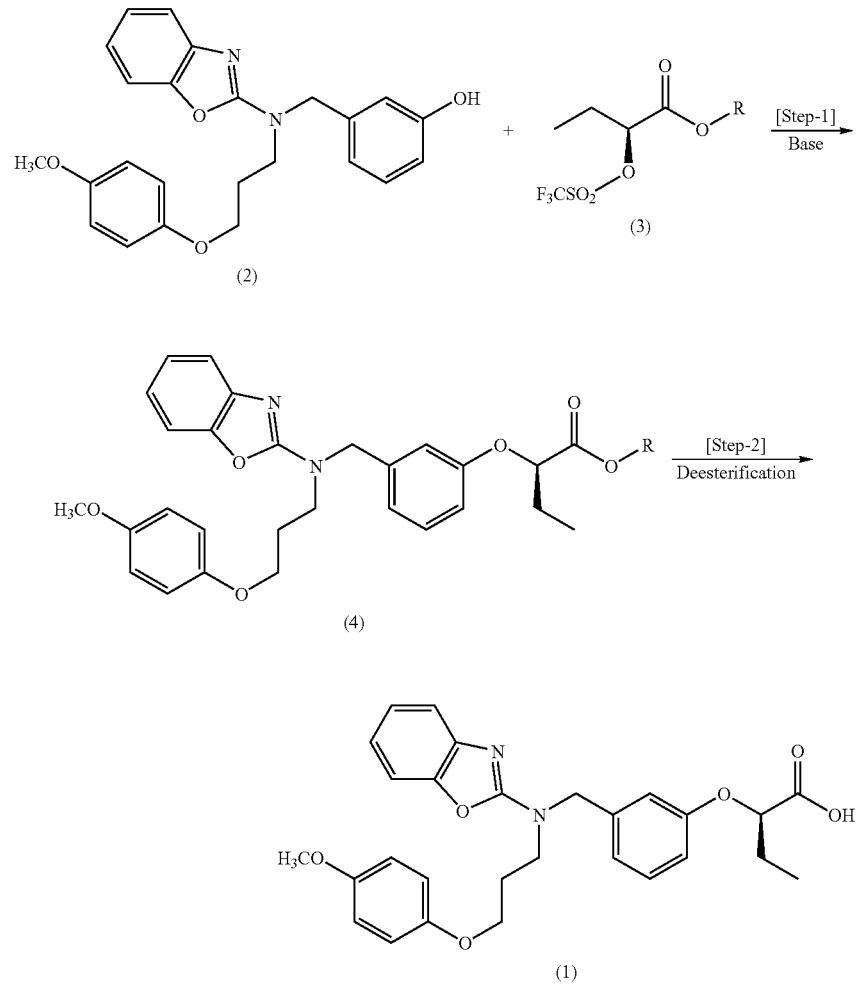

wherein R represents an alkyl group having 1 to 6 carbon atoms, or an aralkyl group having 7 to 8 carbon atoms.

That is, the present invention relates to a process for producing the compound (4), comprising reacting the compound (2) with an optically active 2-trifluoromethanesulfonyloxybutyric acid ester (compound (3)) in the presence of a base.

Furthermore, the present invention relates to a process for producing the compound (1), comprising reacting the compound (2) with an optically active 2-trifluoromethanesulfonyloxybutyric acid ester (compound (3)) in the presence of a base to obtain the compound (4), and then performing deesterification.

The present invention also relates to the compound (4).

Effects of the Invention

According to the process of the present invention, (R)-2-[3-[N-(benzoxazol-2-yl)-N-(3-(4-methoxyphenoxy)propyl)aminomethyl]phenoxy] butyric acid which is a PPARα-selective activator, and which is capable of prevention and/or treatment of hyperlipidemia, arteriosclerosis, diabetes mellitus, diabetic complications, inflammation, heart diseases and the like and an intermediate thereof can be produced in high yield and high optical purity without being accompanied by weight increase and obesity.

BEST MODE FOR CARRYING OUT THE INVENTION

Hereinafter, each of the reaction steps of the process for production of the present invention will be described.

1. Step-1

The present step is a step for producing the compound (4) by reacting the compound (2) and the optically active compound (3) in the presence of a base.

R in the compounds (3) and (4) represents an alkyl group having 1 to 6 carbon atoms or an aralkyl group having 7 to 8 carbon atoms, and the alkyl group is preferably a methyl group, an ethyl group, a n-propyl group, an isopropyl group, a n-butyl group, an isobutyl group, a t-butyl group or the like, while the aralkyl group is preferably a benzyl group, a phenethyl group or the like.

With regard to the base, for example, inorganic bases such as alkali metal hydroxides such as lithium hydroxide, sodium hydroxide, potassium hydroxide and the like; alkali metal carbonates such as sodium carbonate, potassium carbonate, cesium carbonate and the like; alkali metal hydrogen carbonates such as sodium hydrogen carbonate, potassium hydrogen carbonate and the like; organic bases such as pyridine, triethylamine, N,N-diisopropylethylamine, N-methylmorpholine, N,N-dimethylaniline and the like, can be used, but in view of chemical yield, it is preferable to use potassium carbonate.

The present reaction is preferably performed in a solvent. The solvent is not particularly limited, but examples thereof include halogenated hydrocarbons such as methylene chloride, chloroform, carbon tetrachloride, chlorobenzene and the like; aromatic hydrocarbons such as benzene, toluene and the like; ethers such as tetrahydrofuran, diethyl ether, dioxane and the like; ketones such as acetone, methyl ethyl ketone and the like; aprotic polar solvents such as acetonitrile, N,N-dimethylformamide, dimethylsulfoxide and the like; ethyl acetate and the like. Among these, acetonitrile is preferred.

The reaction may be preferably carried out at a reaction temperature of 0 to 100° C., preferably 20 to 90° C., for 0.5 to 48 hours, and preferably for 1 to 24 hours.

PCT/JP04/012750 describes a process related to a phenyl ether formation with a 2-hydroxycarboxylic acid ester, in which a hydroxyl group of a 2-hydroxycarboxylic acid ester is mesylated or tosylated to convert the hydroxyl group to a leaving group such as a methanesulfonyloxy group, a para-toluenesulfonyloxy group or the like, and the leaving group is reacted with a phenol body in the presence of an inorganic base such as sodium carbonate, potassium carbonate, cesium carbonate or the like, or an organic base such as triethylamine, N,N-diisopropylethylamine or the like (Reaction Scheme F-4). In this regard, according to the process of the present invention in which an optically active 2-hydroxybutyric acid ester having a trifluoromethanesulfonyloxy group as a leaving group (compound (3)) is used, the compound (4) can be obtained in extremely high yield and high optical purity (see the Examples described below). Also, the compound is useful as an intermediate of the compound (1).

Here, the compound (2) can be synthesized by, for example, a method shown below.

[Chemical 3]

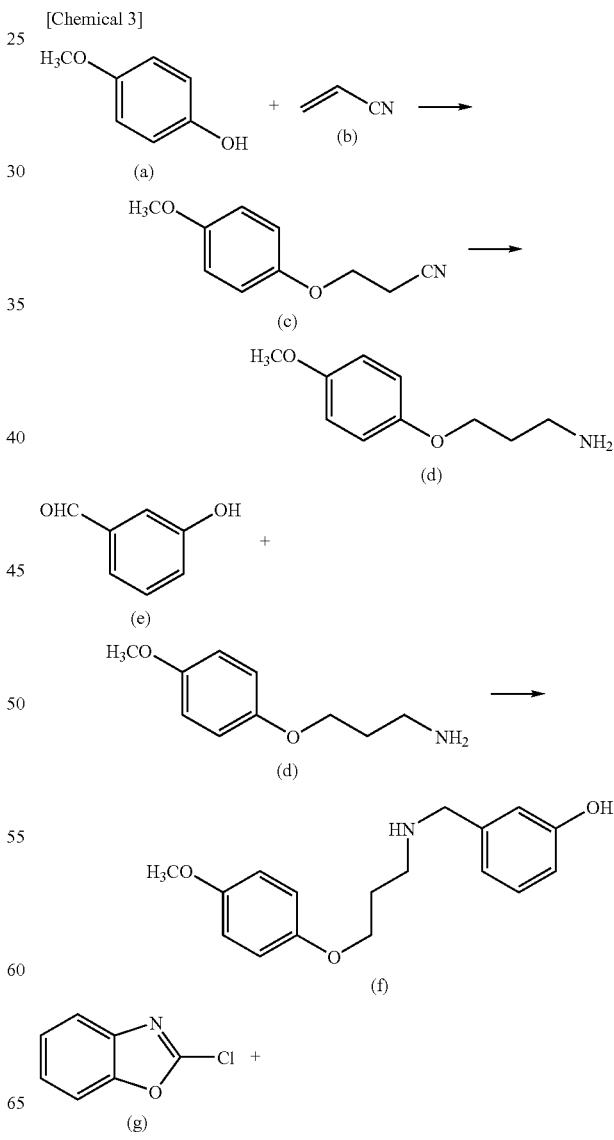

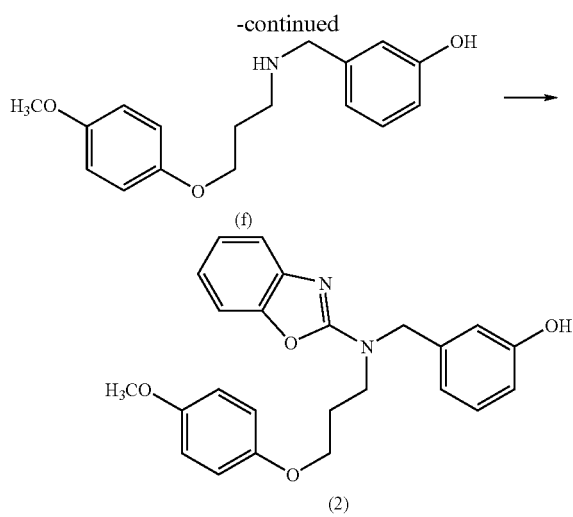

That is, 4-methoxyphenol (a) is reacted with acrylonitrile (b) in the presence of a base such as Triton B, triethylamine, N,N-diisopropylethylamine or the like, at 25 to 120° C. for 1 to 72 hours to obtain 3-(4-methoxyphenoxy)propionitrile (c), and the resultant is either reduced in a solvent such as tetrahydrofuran, dioxane or the like at 25 to 100° C. using a borane-tetrahydrofuran complex, a borane-dimethylsulfide complex, lithium aluminum hydride or the like, or reduced in a hydrogen atmosphere or in the presence of ammonia, using a catalyst such as Raney nickel or the like, thus to obtain 3-(4-methoxyphenoxy)propylamine (d). Subsequently, the resultant is reacted with 3-hydroxybenzaldehyde (e) in a solvent such as methanol, ethanol, isopropyl alcohol, tetrahydrofuran, toluene, acetonitrile or the like, and then the resultant is reduced using a reducing agent such as sodium borohydride, sodium triacetoxy borohydride or the like to obtain N-(3-(4-methoxyphenoxy)propyl)-3-hydroxybenzylamine (f). This is reacted with 2-chlorobenzoxazole (g) in a solvent such as dimethylformamide, acetonitrile, tetrahydrofuran, methylene chloride, chloroform, ethyl acetate or the like, in the presence of an inorganic base such as sodium carbonate, potassium carbonate, cesium carbonate or the like, or an organic base such as triethylamine, N,N-diisopropylethylamine, pyridine or the like, thus to obtain N-(benzoxazol-2-yl)-N-(3-(4-methoxyphenoxy)propyl)-3-hydroxybenzylamine (compound (2)).

Furthermore, the compound (3) can be synthesized, as shown below for example, by reacting a (S)-2-hydroxybutyric acid ester (h) with trifluoromethanesulfonic anhydride (i) in a solvent such as methylene chloride, chloroform, carbon tetrachloride, tetrahydrofuran, toluene, hexane or the like, at −80 to 30° C. for 10 minutes to 3 hours.

[Chemical 4]

wherein R represents an alkyl group having 1 to 6 carbon atoms or an aralkyl group having 7 to 8 carbon atoms.

2. Step-2

The present step is a step for producing the compound (1) by deesterifying an ester of the compound (4).

The deesterification reaction can be performed by a standard method such as hydrolysis, hydrogenolysis (reduction). The hydrolysis can be performed by applying all of the reaction conditions that are used in a hydrolysis reaction of ester, and for example, it is performed in the presence of inorganic base such as lithium hydroxide, sodium hydroxide, potassium hydroxide, sodium carbonate, potassium carbonate or the like; a mineral acid such as hydrochloric acid, sulfuric acid, hydrobromic acid or the like; or an organic acid such as p-toluenesulfonic acid or the like, in a solvent such as water, an alcohol such as methanol, ethanol, propanol or the like, an ether such as tetrahydrofuran, dioxane or the like, a ketone such as acetone, methyl ethyl ketone or the like, acetic acid, or a solvent mixture thereof.

The reaction is performed usually at 0 to 100° C., and preferably 10 to 50° C., and the reaction time is usually 0.5 to 24 hours, and preferably 1 to 12 hours.

The hydrogenolysis is performed, for example, in an inert solvent (for example, an ether such as tetrahydrofuran, dioxane, dimethoxyethane, diethyl ether or the like; an alcohol such as methanol, ethanol, isopropyl alcohol or the like; an amide such as dimethylformamide or the like), in the presence of a hydrogenating catalyst (for example, palladium-carbon, palladium black, palladium, palladium hydroxide, platinum-carbon, platinum dioxide, Raney nickel or the like), in the presence or absence of an inorganic acid (for example, hydrochloric acid, sulfuric acid, hypochlorous acid or the like) or an organic acid (for example, acetic acid, trifluoroacetic acid, formic acid or the like), in a hydrogen atmosphere at ambient pressure or under pressure.

The reaction is performed usually at 0 to 30° C., and preferably 10 to 25° C., and the reaction time is usually 5 minutes to 24 hours, and preferably 1 to 12 hours.

In the present step, the compound (1) can be obtained in high yield without impairing the optical purity of the compound (4).

Furthermore, separation of the target product in each reaction of the present invention may be performed, if necessary, by purification methods that are conventionally used in organic synthetic chemistry, for example, by filtration, washing, drying, recrystallization, various chromatographies and the like.

EXAMPLES

Hereinafter, the present invention will be described in more detail with reference to Examples.

Preparative Example 1

Synthesis of 3-(4-methoxyphenoxy)propionitrile

[Chemical 5]

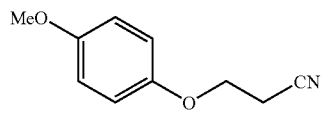

4-Methoxyphenol (263.0 g) was dissolved in acrylonitrile (224.8 g), and then Triton B (18 mL) was added dropwise at room temperature, with stirring at 80° C. for 48 hours. The reaction liquor was returned to room temperature while slowly stirring, and stirred for 12 hours. The reaction liquor was further left to stand at 6° C. to precipitate white prisms. The mother liquor was subjected to decantation, and cold toluene (300 mL) was added to obtain crystals, and then the resulting crude crystals were dried at room temperature under reduced pressure (3 hours) (crude crystals 232.6 g). The crude crystals were dissolved in ethyl acetate (250 mL) at 50° C., n-heptane (250 mL) was slowly added with stirring, and the resulting mixture was recrystallized with slow stirring for 12 hours. The mother liquor was subjected to decantation, n-heptane (300 mL) was added, and crystals were obtained. The crystals were washed with n-heptane (400 mL) and dried at room temperature under reduced pressure (crystal No. 1: white prisms 154.5 g). Since crystals were generated in the mother liquor, pale yellow prisms were obtained as crystal No. 2 (crystal No. 2: pale yellow prisms 56.1 g). All of the filtrate and n-heptane used for washing were recovered and concentrated under reduced pressure. Then, toluene (500 mL) was added to the residue, and the mixture was washed with 1 N aqueous sodium hydroxide solution (100 mL×3 times), water (500 mL), 1 N aqueous hydrochloric acid solution (100 mL×3 times), water (500 mL) and saturated brine (300 mL), then dried over anhydrous sodium sulfate for 30 minutes, and filtered, and subsequently the filtrate was concentrated under reduced. The residue was dissolved in ethyl acetate (150 mL) at 50° C., and n-heptane (150 mL) was slowly added with stirring, and the resulting mixture was recrystallized with slow stirring for 12 hours. The mother liquor was subjected to decantation, and n-heptane (200 mL) was added, and crystals were obtained. The crystals were washed with n-heptane (300 mL) and dried at room temperature under reduced pressure (crystal No. 3: white prisms 59.0 g). Furthermore, pale yellow prisms were obtained as crystal No. 4 (crystal No. 4: 19.0 g). Total amount obtained was 288.6 g, yield was 76.9%+ crude crystals (yellow prisms, 21.8 g, 5.8%).

$^1$H-NMR (400 MHz, CDCl$_3$) δ: 2.79 (t, J=7 Hz, 2H), 3.77 (s, 3H), 4.15 (t, J=7 Hz, 2H), 6.85 (d, J=7 Hz, 4H).

Melting point: 64.4° C.

Preparative Example 2

Synthesis of 3-(4-methoxyphenoxy)propylamine

[Chemical 6]

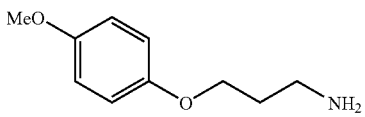

Under an argon atmosphere, 3-(4-methoxyphenoxy)propionitrile (5.0 g) was dissolved in tetrahydrofuran (20 mL), and borane-tetrahydrofuran complex (1.02 mol/L, 30.0 mL) was added dropwise at 80° C. for 10 minutes. After stirring for 3 hours at the same temperature, the reaction liquor was returned to room temperature. In an ice-cold bath, a 4 N aqueous sodium hydroxide solution (30 mL) was added for 10 minutes. After 10 minutes, the mixture was stirred at room temperature for 5 minutes, and then stirred at 80° C. for 12 hours. The mixture was returned to room temperature, and toluene (100 mL) was added, and the mixture was stirred for 1 hour, and then insoluble material was removed using Celite. An organic layer was isolated, and washed with water (100 mL×2 times) and saturated brine (100 mL), and then dried over anhydrous sodium sulfate (80 g). The resultant was filtered, and then the filtrate was concentrated under reduced pressure to obtain a white solid (4.0 g, 79.0%).

$^1$H-NMR (400 MHz, CD$_3$OD) δ: 2.05 (quintet, J=7 Hz, 2H), 3.07 (t, J=7 Hz, 2H), 3.71 (s, 3H), 4.01 (t, J=6 Hz, 2H), 6.79-6.85 (m, 4H).

Preparative Example 3

Synthesis of N-(3-(4-methoxyphenoxy)propyl)-3-hydroxybenzylamine

[Chemical 7]

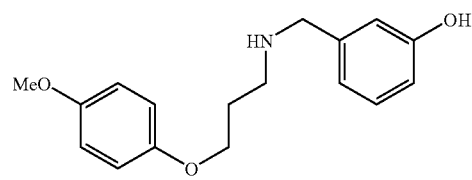

3-(4-Methoxyphenoxy)propylamine (10.0 g) was dissolved in methanol (50 mL) at room temperature, a solution of 3-hydroxybenzaldehyde (6.7 g) in methanol (50 mL) was added dropwise within 5 minutes at water temperature (about 20° C.), and then the resulting mixture was stirred at room temperature for 20 hours. Then, sodium borohydride (2.1 g)/water (100 mL) was added dropwise at water temperature (about 20° C.) for 5 minutes, and the mixture was stirred at room temperature for 12 hours. Precipitates were removed, washed with water and then dried under reduced pressure at 80° C. for 5 hours. Pale yellow crystals were obtained (13.9 g, 87.4%).

$^1$H-NMR (400 MHz, DMSO-d$_6$) δ: 1.82 (quintet, J=7 Hz, 2H), 2.60 (t, J=7 Hz, 2H), 3.60 (s, 2H), 3.68 (s, 3H), 3.95 (t, J=7 Hz, 2H), 6.60 (d, J=8 Hz, 1H), 6.73 (t, J=8 Hz, 1H), 6.74 (s, 1H), 6.83 (s, 4H), 7.07 (t, J=8 Hz, 1H).

Melting point: 142.7° C.

Preparative Example 4

Synthesis of N-(benzoxazol-2-yl)-N-(3-(4-methoxyphenoxy)propyl)-3-hydroxybenzylamine

[Chemical 8]

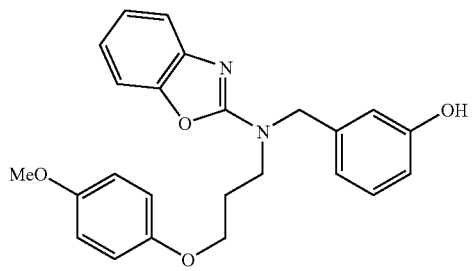

N-(3-(4-methoxyphenoxy)propyl)-3-hydroxybenzylamine (1.0 g) was suspended in dimethylformamide (4 mL) at room temperature, and triethylamine (387 mg) was further added and was completely dissolved. 2-Chlorobenzoxazole (534 mg) was added dropwise at 80° C. The mixture was stirred at 80° C. for 4 hours, and then the reaction liquor was returned to room temperature. The solvent was distilled off, then ethyl acetate was added, and the mixture was washed with water and saturated brine and then dried over anhydrous sodium sulfate. The resultant was concentrated under reduced pressure, and then the residue was purified by silica gel column chromatography (hexane/ethyl acetate=3/1) to obtain a yellow oil (1.4 g, 98.8%). To the resulting yellow oil, tert-Butyl methyl ether (4 mL) was added to crystallize, and then the crystals were collected by filtration and washed with cyclohexane. Then, the crystals were dried at room temperature for 5 hours to obtain white crystals (1.3 g, 92.2%).

$^1$H-NMR (400 MHz, CDCl$_3$) δ: 1.98 (quintet, J=7 Hz, 2H), 3.37 (t, J=7 Hz, 2H), 3.75 (s, 3H), 3.86 (t, J=6 Hz, 2H), 4.61 (s, 2H), 6.65-6.81 (m, 7H), 6.90-7.13 (m, 5H)

Melting point: 104.3° C.

Preparative Example 5

Synthesis of benzyl (S)-2-trifluoromethanesulfonyloxybutyrate

[Chemical 9]

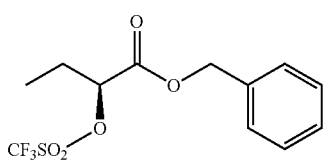

Benzyl (S)-2-hydroxybutyrate (758 mg, 99% ee) was dissolved in methylene chloride (10 mL), and pyridine (324 mg) was added. Then, trifluoromethanesulfonic anhydride (1.10 g, 3.90 mmol) was added dropwise at 0° C. and stirred for 30 minutes. After the reaction, the reaction liquor was subjected to silica gel column chromatography, eluted with chloroform, and then concentrated under reduced pressure, to obtain a colorless oil (1.2 g, 96.0%).

$^1$H-NMR (400 MHz, CDCl$_3$) δ: 1.02 (t, J=7 Hz, 3H), 2.00-2.09 (m, 2H), 5.11 (dd, J=5, 7 Hz, 1H), 5.25 (dd, J=12, 16 Hz, 2H), 7.33-7.39 (m, 5H).

Example 1

Synthesis of benzyl (R)-2-[3-[N-(benzoxazol-2-yl)-N-(3-(4-methoxyphenoxy)propyl)aminomethyl]phenoxy]butyrate

[Chemical 10]

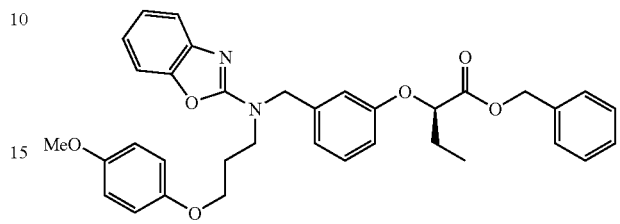

To a solution of N-(benzoxazol-2-yl)-N-(3-(4-methoxyphenoxy)propyl)-3-hydroxybenzylamine (52 mg) in acetonitrile (5 mL), potassium carbonate (18 mg) in a powder form was added at room temperature, and the resulting mixture was stirred for 10 minutes. A solution of benzyl (S)-2-trifluoromethanesulfonyloxybutyrate (50 mg) in acetonitrile (2 mL) was added dropwise to the reaction liquor, and the mixture was stirred at the same temperature for 18 hours. Ethyl acetate (50 mL) was added to the reaction liquor, and the mixture was washed with water and saturated brine, and dried over anhydrous sodium sulfate. After filtration, the filtrate was concentrated under reduced pressure, and the residue was purified by silica gel column chromatography (hexane/ethyl acetate=2/1) to obtain a colorless oil (73 mg, 98.3%).

$^1$H-NMR (400 MHz, CDCl$_3$) δ: 1.01 (t, J=7 Hz, 3H), 1.95 (quintet, J=7 Hz, 2H), 2.11 (quintet, J=7 Hz, 2H), 3.66 (t, J=7 Hz, 2H), 3.73 (s, 3H), 3.93 (t, J=6 Hz, 2H), 4.56 (t, J=6 Hz, 1H), 4.70 (s, 2H), 5.09 (q, J=13 Hz, 2H), 6.70-6.90 (m, 7H), 6.99 (td, J=1, 8 Hz, 1H), 7.17-7.34 (m, 9H).

Example 2

Synthesis of (R)-2-[3-[N-(benzoxazol-2-yl)-N-(3-(4-methoxyphenoxy)propyl)aminomethyl]phenoxy]butyric acid

[Chemical 11]

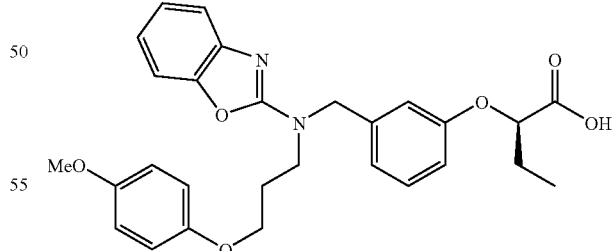

Benzyl (R)-2-[3-[N-(benzoxazol-2-yl)-N-(3-(4-methoxyphenoxy)propyl)aminomethyl]phenoxy]butyrate (72 mg) was dissolved in ethanol (3 mL), and a 4 N aqueous sodium hydroxide solution (0.5 mL) was added at 0° C. Then, the resulting mixture was stirred at room temperature for 1 hour. The reaction liquor was concentrated under reduced pressure, and then was dissolved in chloroform (30 mL). The solution was washed with a saturated aqueous solution of ammonium chloride and dried over anhydrous sodium sulfate. After filtration, the filtrate was concentrated under reduced pressure, and the residue was purified by preparative TLC (chloroform/methanol=10/1) to obtain a colorless solid (61 mg, 100%).

1H-NMR (400 MHz, CD$_3$OD) δ: 0.94 (t, J=7.4 Hz, 3H), 1.81 (m, 2H), 1.99 (quintet, J=6.1 Hz, 2H), 3.60 (t, J=6.8 Hz, 2H), 3.61 (s, 3H), 3.85 (t, J=5.9 Hz, 2H), 4.40 (t, J=5.9 Hz, 1H), 4.65 (s, 2H), 6.69-6.80 (m, 7H), 6.91 (dt, J=7.2, 1.0 Hz, 1H), 7.05 (dt, J=7.2, 1.2 Hz, 1H), 7.12-7.18 (m, 4H).

Optical purity: 99% ee
Measurement conditions: HPLC
Column: CHIRALCEL OD
Solvent: hexane/isopropyl alcohol/trifluoroacetic acid=60/40/0.1
Flow rate: 1 mL/min
Maintenance time: R-isomer; 13.3 min (S-isomer: 7.9 min)

Preparative Example 6

Synthesis of n-butyl (S)-2-trifluoromethanesulfonyloxybutyrate

[Chemical 12]

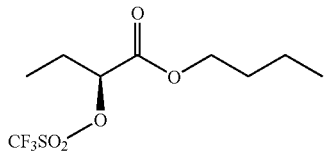

n-Butyl (S)-2-hydroxybutyrate (300 mg, 99% ee) was dissolved in methylene chloride (5 mL), and pyridine (155 mg) was added at 0° C. Then, trifluoromethanesulfonic anhydride (528 mg) was added dropwise at 0° C., and the resulting mixture was stirred for 30 minutes. The reaction liquor was subjected to silica gel column chromatography and eluted with chloroform, and then a colorless oily product was obtained (587 mg). The total amount was directly used in the next reaction.

$^1$H-NMR (400 MHz, CDCl$_3$) δ: 0.93 (t, J=7 Hz, 3H), 1.05 (t, J=7 Hz, 3H), 1.34-1.43 (m, 2H), 1.65 (quintet, J=7 Hz, 3H), 1.97-2.08 (m, 2H), 4.23 (td, J=7, 3 Hz, 2H), 5.06 (dd, J=7, 5 Hz, 1H).

Example 3

Synthesis of n-butyl (R)-2-[3-[N-(benzoxazol-2-yl)-N-(3-(4-methoxyphenoxy)propyl)aminomethyl]phenoxy]butyrate

[Chemical 13]

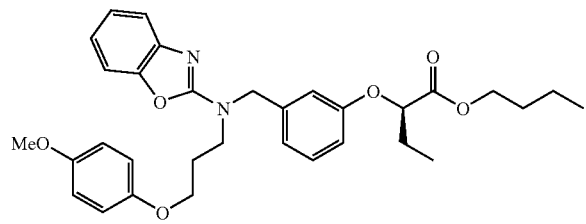

To a solution of N-(benzoxazol-2-yl)-N-(3-(4-methoxyphenoxy)propyl)-3-hydroxybenzylamine (530 mg) in acetonitrile (10 mL), potassium carbonate (272 mg) in a powder form was added at room temperature, and the resulting mixture was stirred for 10 minutes. The solution of n-butyl (S)-2-trifluoromethanesulfonyloxybutyrate (587 mg) in acetonitrile (10 mL) prepared in Preparative Example 6 was added to the reaction solution, and the mixture was stirred at room temperature for 14 hours. Water was added to the reaction solution, the mixture was extracted with toluene, and the extract was washed with saturated brine and dried over anhydrous sodium sulfate. The solution was filtered and concentrated under reduced pressure, and then the residue was purified by silica gel column chromatography (hexane/ethyl acetate=2/1) to obtain a colorless oil (748 mg, 100%).

$^1$H-NMR (400 MHz, CDCl$_3$) δ: 0.83 (t, J=7 Hz, 3H), 1.03 (t, J=7 Hz, 3H), 1.18-1.29 (m, 2H), 1.44-1.55 (m, 2H), 1.93 (quintet, J=7 Hz, 2H), 2.12 (quintet, J=7 Hz, 2H), 3.67 (t, J=7 Hz, 2H), 3.74 (s, 3H), 3.94 (t, J=6 Hz, 2H), 3.98-4.13 (m, 2H), 4.51 (t, J=6 Hz, 1H), 4.72 (d, J=3 Hz, 2H), 6.74 (dd, J=8, 2 Hz, 1H), 6.78 (s, 4H), 6.84 (t, J=2 Hz, 1H), 6.88 (d, J=8 Hz, 1H), 6.99 (td, J=8, 1 Hz, 1H), 7.14 (td, J=8, 1 Hz, 2H), 7.19-7.24 (m, 3H), 7.34 (dd, J=8, 1 Hz, 1H).

Example 4

Synthesis of (R)-2-[3-[N-(benzoxazol-2-yl)-N-(3-(4-methoxyphenoxy)propyl)aminomethyl]phenoxy]butyric acid

[Chemical 14]

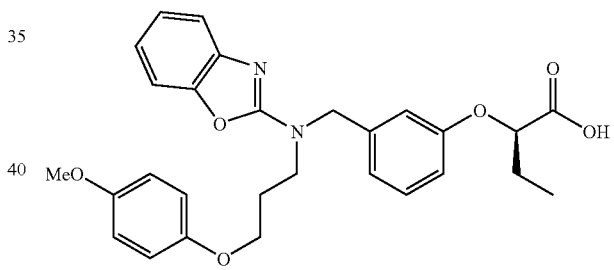

n-Butyl (R)-2-[3-[N-(benzoxazol-2-yl)-N-(3-(4-methoxyphenoxy)propyl)aminomethyl]phenoxyl]butyrate (68 mg) was dissolved in ethanol (2 mL), and a 4 N aqueous sodium hydroxide solution (0.2 mL) was added at 0° C. Then, the resulting mixture was stirred at room temperature for 3 hours. Ethanol was distilled off, and water was added, and then the reaction liquor was acidified with concentrated hydrochloric acid in an ice-cold bath. The reaction liquor was extracted with ethyl acetate, and the extract was washed with water and saturated brine, and dried over dry sodium sulfate. The solution was filtered and concentrated under reduced pressure, and then the residue was purified by silica gel column chromatography (chloroform/methanol=10/1) to obtain a colorless solid (60 mg, 100%).

Optical purity: 99% ee
Measurement conditions: HPLC
Column: CHIRALCEL OD
Solvent: hexane/isopropyl alcohol/trifluoroacetic acid=60/40/0.1
Flow rate: 1 mL/min Maintenance time: R-isomer; 13.3 min (S-isomer; 7.9 min)

Examples 5 to 11, Comparative Example 1 to 8

In the same manner as in Examples 1 and 2, a phenyl etherification reaction (step-1) and hydrolysis (step-2) were performed under the conditions indicated in the following Table 1. Also, phenethyl (S)-2-trifluoromethanesulfonyloxybutyrate (Example 11) and phenethyl (S)-2-para-toluenesulfonyloxybutyrate (Comparative Example 7) were produced using (S)-2-hydroxybutyric acid, n-butyl (S)-2-methanesulfonyloxybutrate (Comparative Examples 1 to 3) and n-butyl (S)-2-para-toluenesulfonyloxybutyrate (Comparative Examples 4 to 6) were produced using n-butyl (S)-2-hydroxybutrate, and methyl (S)-2-chlorobutyrate (Comparative Example 8) was produced using (S)-2-chlorobutyric acid, according to standard methods. The yields and optical purities are presented together in Table 1.

TABLE 1

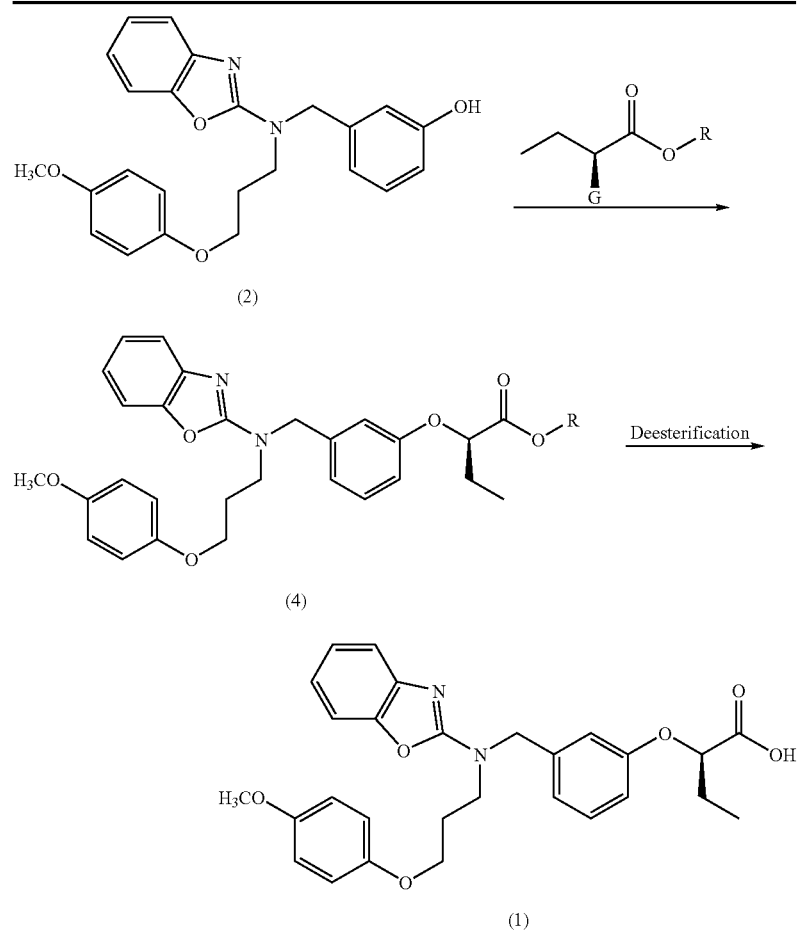

| No. | R | G | Base | Solvent | Temp.(° C.) | Time(h) | C.Y.(%) | O.Y.(% ee) |
|---|---|---|---|---|---|---|---|---|
| Ex. 1 | PhCH$_2$ | CF$_3$SO$_3$ | K$_2$CO$_3$ | MeCN | r.t. | 18 | 98 | 99 |
| Ex. 3 | n-Bu | CF$_3$SO$_3$ | K$_2$CO$_3$ | MeCN | r.t. | 14 | 100 | 99 |
| Ex. 5 | n-Bu | CF$_3$SO$_3$ | K$_2$CO$_3$ | MeCN | 30 | 8 | 99 | 99 |
| Ex. 6 | n-Bu | CF$_3$SO$_3$ | K$_2$CO$_3$ | MeCN | 40 | 5.5 | 100 | 99 |
| Ex. 7 | n-Bu | CF$_3$SO$_3$ | K$_2$CO$_3$ | MeCN | 50 | 3 | 100 | 99 |
| Ex. 8 | n-Bu | CF$_3$SO$_3$ | K$_2$CO$_3$ | MeCN | 60 | 6 | 100 | 98 |
| Ex. 9 | n-Bu | CF$_3$SO$_3$ | K$_2$CO$_3$ | MeCN | 90 | 6 | 100 | 94 |
| Ex. 10 | n-Bu | CF$_3$SO$_3$ | Et$_3$N | CHCl$_3$ | r.t. | 48 | 80 | 99 |
| Ex. 11 | Ph(CH$_2$)$_2$ | CF$_3$SO$_3$ | K$_2$CO$_3$ | MeCN | r.t. | 24 | 97 | 99 |
| Comp. Ex. 1 | n-Bu | MsO | K$_2$CO$_3$ | MeCN | r.t. | 55 | 59 | 97 |
| Comp. Ex. 2 | n-Bu | MsO | K$_2$CO$_3$ | MeCN | 60 | 24 | 93 | 75 |
| Comp. Ex. 3 | n-Bu | MsO | Cs$_2$CO$_3$ | MeCN | r.t. | 27 | 90 | 74 |
| Comp. Ex. 4 | n-Bu | TsO | K$_2$CO$_3$ | MeCN | r.t. | 24 | 10 | 100 |
| Comp. Ex. 5 | n-Bu | TsO | K$_2$CO$_3$ | MeCN | 60 | 24 | 69 | 91 |

TABLE 1-continued

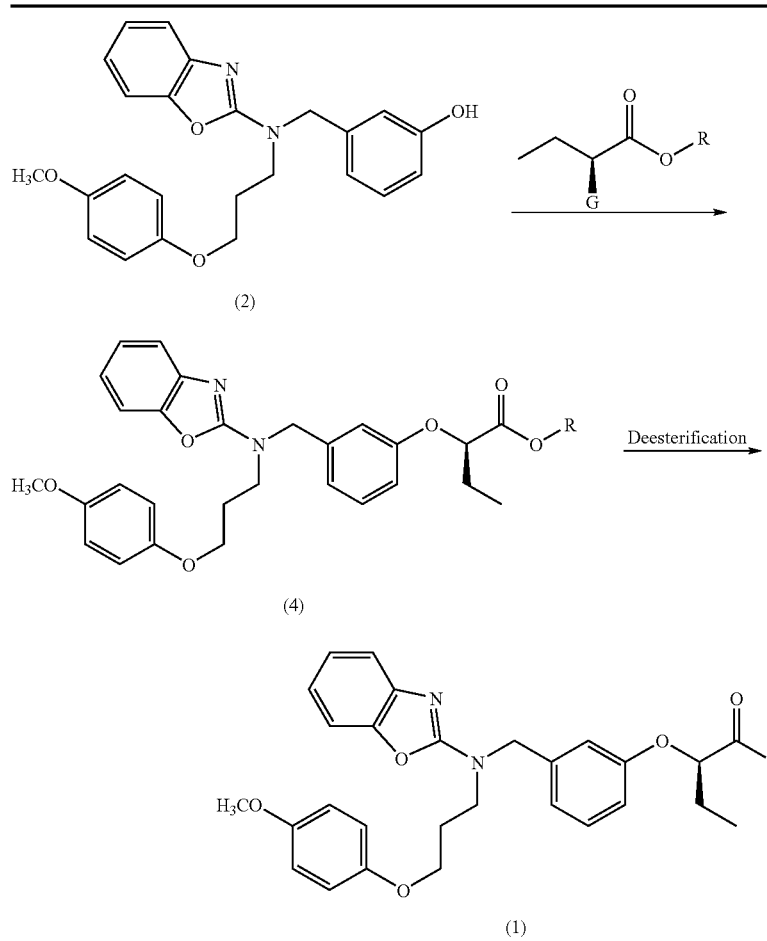

| No. | R | G | Base | Solvent | Temp.(° C.) | Time(h) | C.Y.(%) | O.Y.(% ee) |
|---|---|---|---|---|---|---|---|---|
| Comp. Ex. 6 | n-Bu | TsO | Cs$_2$CO$_3$ | MeCN | r.t. | 24 | 77 | 92 |
| Comp. Ex. 7 | Ph(CH$_2$)$_2$ | TsO | K$_2$CO$_3$ | MeCN | 60 | 48 | 73 | 92 |
| Comp. Ex. 8 | Me | Cl | K$_2$CO$_3$ | MeCN | 60 | 48 | 38 | 13 |

C.Y. = Chemical yield of compound (4)
O.Y. = Optical purity of compound (1)

In the method of using a butyric acid ester in which G is a trifluoromethanesulfonyloxy group (Examples 1 to 11), the chemical yields and the optical yields were high, while in the case of using other butyric acid esters, the result of both the chemical yield and the optical yield being high could not be obtained.

From the above, the present invention is an excellent method which can provide (R)-2-[3-[N-(benzoxazol-2-yl)-N-(3-(4-methoxyphenoxy)propyl)aminomethyl]phenoxy]butyric acid and an intermediate thereof in high yield and high optical yield.

The invention claimed is:

1. A process for producing a compound represented by the following Formula (4):

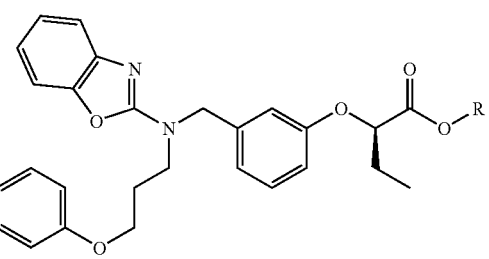

wherein R is an alkyl group having 1 to 6 carbon atoms or an aralkyl group having 7 to 8 carbon atoms, the process comprising reacting a compound represented by the following Formula (2):

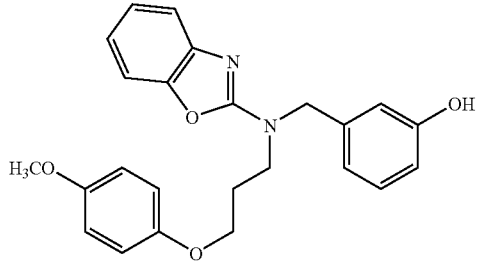

with an optically active 2-trifluoromethanesulfonyloxy-butyric acid ester represented by the following Formula (3):

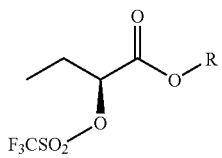

wherein R has the same meaning as defined above, in the presence of a base.

2. A process for producing a compound represented by the following Formula (1):

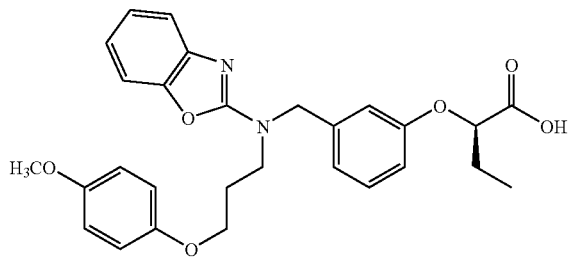

the process comprising reacting a compound represented by the following Formula (2):

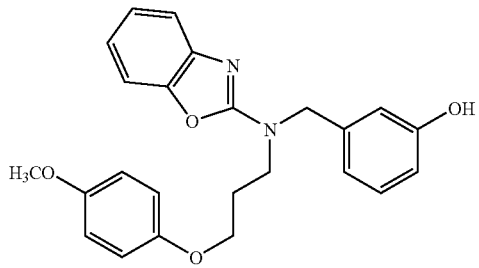

with an optically active 2-trifluoromethanesulfonyloxy-butyric acid ester represented by the following Formula (3):

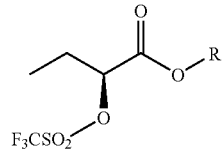

wherein R represents an alkyl group having 1 to 6 carbon atoms or an aralkyl group having 7 to 8 carbon atoms, in the presence of a base to obtain a compound represented by the following Formula (4):

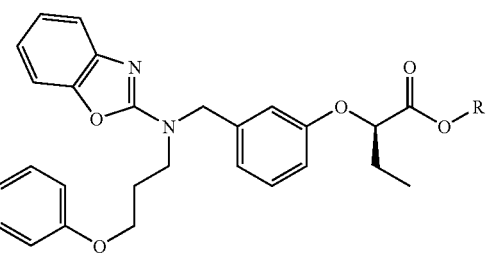

wherein R has the same meaning as defined above, and then deesterifying the resulting compound.

3. A compound represented by the following Formula (4):

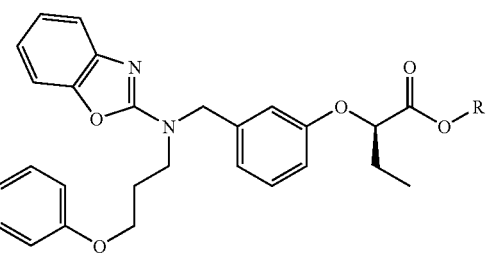

wherein R represents an alkyl group having 1 to 6 carbon atoms or an aralkyl group having 7 to 8 carbon atoms.

4. The process according to claim 1, wherein R is an alkyl group having 1 to 6 carbon atoms.

5. The process according to claim 1, wherein R is an alkyl group having 1 to 6 carbon atoms which is selected from the group consisting of methyl, ethyl, n-propyl, isopropyl, n-butyl, isobutyl and t-butyl.

6. The process according to claim 1, wherein said base is at least one base selected from the group consisting of lithium hydroxide, sodium hydroxide, potassium hydroxide, sodium carbonate, potassium carbonate, cesium carbonate, sodium hydrogen carbonate, potassium hydrogen carbonate, pyridine, triethylamine, N,N-diisopropylethylamine, N-methylmorpholine and N,N-dimethylaniline.

7. The process according to claim 1, wherein said compounds of formula (2) and formula (3) are reacted at a temperature of from 20 to 90° C.

8. The process according to claim 1, wherein said compound of formula (3) has an optical purity of 99% ee.

9. The process according to claim 1, wherein said compound of formula (4) has an optical purity of from 94-99% ee.

10. The process according to claim 2, wherein R is an alkyl group having 1 to 6 carbon atoms.

11. The process according to claim 2, wherein R is an alkyl group having 1 to 6 carbon atoms which is selected from the group consisting of methyl, ethyl, n-propyl, isopropyl, n-butyl, isobutyl and t-butyl.

12. The process according to claim 2, wherein said base is at least one base selected from the group consisting of lithium hydroxide, sodium hydroxide, potassium hydroxide, sodium carbonate, potassium carbonate, cesium carbonate, sodium hydrogen carbonate, potassium hydrogen carbonate, pyridine, triethylamine, N,N-diisopropylethylamine, N-methylmorpholine and N,N-dimethylaniline.

13. The process according to claim 2, wherein said compounds of formula (2) and formula (3) are reacted at a temperature of from 20 to 90° C.

14. The process according to claim 2, wherein said compound of formula (3) has an optical purity of 99% ee.

15. The process according to claim 2, wherein said compound of formula (1) has an optical purity of from 94-99% ee.

\* \* \* \* \*